US011272594B2

(12) United States Patent
Yadav et al.

(10) Patent No.: US 11,272,594 B2
(45) Date of Patent: Mar. 8, 2022

(54) MULTI-ARRAY LIGHTING SYSTEM FOR PROVIDING HIGH INTENSITY NARROW SPECTRUM LIGHT

(71) Applicant: Hubbell Incorporated, Shelton, CT (US)

(72) Inventors: Pritam Yadav, Greenville, SC (US); Douglas M. Hamilton, Arlington Heights, IL (US); Christopher Lane Bailey, Greenville, SC (US)

(73) Assignee: Hubbell Incorporated, Shelton, CT (US)

( * ) Notice: Subject to any disclaimer, the term of this patent is extended or adjusted under 35 U.S.C. 154(b) by 0 days.

(21) Appl. No.: 15/797,760

(22) Filed: Oct. 30, 2017

(65) Prior Publication Data

US 2018/0117193 A1    May 3, 2018

Related U.S. Application Data

(60) Provisional application No. 62/414,987, filed on Oct. 31, 2016.

(51) Int. Cl.
*A61L 2/10* (2006.01)
*H05B 45/30* (2020.01)
(Continued)

(52) U.S. Cl.
CPC ............... *H05B 45/30* (2020.01); *A61L 2/08* (2013.01); *A61L 2/10* (2013.01); *F21V 19/001* (2013.01);
(Continued)

(58) Field of Classification Search
CPC ........ F21Y 2113/00–20; F21Y 2113/13; A61L 2/08–12
See application file for complete search history.

(56) References Cited

U.S. PATENT DOCUMENTS 3,926,556 A   12/1975   Boucher
4,910,942 A   3/1990    Dunn et al.
(Continued)

FOREIGN PATENT DOCUMENTS

JP   2004301387   10/2004
JP   2007232323   9/2007
(Continued)

OTHER PUBLICATIONS

Maclean et al., "405 nm light technology for the inactivation of pathogens and its potential role for environmental disinfection and infection control," *The Journal of Hospital Infection*, Sep. 2014, vol. 88, Issue 1—27 pages.
(Continued)

*Primary Examiner* — Sean P Gramling
(74) *Attorney, Agent, or Firm* — Michael Best & Friedrich LLP

(57) ABSTRACT

Multisource LED systems for providing high intensity narrow spectrum light are provided. In one example embodiment, a lighting system includes one or more first light sources configured to emit high intensity narrow spectrum (HINS) light. The lighting system can include one or more second light sources configured to emit non-HINS light. The system can include a power circuit configured to provide power to the one or more first light sources and the one or more second light sources.

18 Claims, 6 Drawing Sheets

(51) Int. Cl.
| | |
|---|---|
| *F21V 23/02* | (2006.01) |
| *F21V 19/00* | (2006.01) |
| *A61L 2/08* | (2006.01) |
| F21Y 115/10 | (2016.01) |
| F21Y 113/13 | (2016.01) |
| H05B 45/31 | (2020.01) |
| H05B 45/325 | (2020.01) |

(52) U.S. Cl.
CPC ........... *F21V 23/02* (2013.01); *F21Y 2113/13* (2016.08); *F21Y 2115/10* (2016.08); *H05B 45/31* (2020.01); *H05B 45/325* (2020.01)

(56) References Cited

U.S. PATENT DOCUMENTS

| | | | |
|---|---|---|---|
| 6,251,127 B1 | 6/2001 | Biel | |
| 8,398,264 B2 | 3/2013 | Anderson et al. | |
| 9,016,892 B1* | 4/2015 | Scribante | F21V 17/002 362/222 |
| 9,039,966 B2 | 5/2015 | Anderson et al. | |
| 9,333,274 B2 | 5/2016 | Peterson et al. | |
| 9,439,989 B2 | 9/2016 | Lalicki | |
| 9,642,356 B2 | 5/2017 | Wood et al. | |
| 9,642,358 B2 | 5/2017 | Cai et al. | |
| 9,700,641 B2 | 7/2017 | Hawkins et al. | |
| 9,927,097 B2 | 3/2018 | Lalicki et al. | |
| 2002/0074559 A1 | 6/2002 | Dowling et al. | |
| 2003/0137258 A1 | 7/2003 | Piepgras et al. | |
| 2004/0008523 A1* | 1/2004 | Butler | A61N 5/0613 362/551 |
| 2004/0039242 A1 | 2/2004 | Tolkoff et al. | |
| 2004/0141321 A1 | 7/2004 | Dowling et al. | |
| 2005/0049228 A1 | 3/2005 | Albrecht et al. | |
| 2005/0055070 A1 | 3/2005 | Jones et al. | |
| 2005/0107849 A1 | 5/2005 | Altshuler et al. | |
| 2006/0085052 A1 | 4/2006 | Feuerstein et al. | |
| 2006/0221606 A1 | 10/2006 | Dowling et al. | |
| 2007/0109763 A1* | 5/2007 | Wolf | A01M 1/2083 362/86 |
| 2008/0137066 A1 | 6/2008 | Weinstein | |
| 2009/0076115 A1 | 3/2009 | Wharton et al. | |
| 2009/0168396 A1* | 7/2009 | Moriyasu | H05B 33/0803 362/84 |
| 2010/0208054 A1 | 8/2010 | Farr | |
| 2010/0246169 A1 | 9/2010 | Anderson | |
| 2010/0259917 A1 | 10/2010 | Ramer et al. | |
| 2011/0180687 A1 | 7/2011 | Rains, Jr. et al. | |
| 2011/0227487 A1 | 9/2011 | Nichol et al. | |
| 2011/0256019 A1 | 10/2011 | Gruen et al. | |
| 2013/0291735 A1 | 11/2013 | Livchak et al. | |
| 2013/0293156 A1 | 11/2013 | Wells | |
| 2014/0060096 A1 | 3/2014 | Shur | |
| 2014/0278136 A1 | 9/2014 | Shamsheyeva et al. | |
| 2015/0002027 A1 | 1/2015 | Huang | |
| 2015/0273092 A1 | 10/2015 | Holub et al. | |
| 2016/0015840 A1 | 1/2016 | Gordon | |
| 2016/0030609 A1* | 2/2016 | Peterson | A61L 2/08 362/84 |
| 2016/0030610 A1 | 2/2016 | Peterson et al. | |
| 2016/0120410 A1 | 5/2016 | Kim | |
| 2016/0339203 A1 | 11/2016 | Krames et al. | |
| 2016/0361229 A1 | 12/2016 | Na | |
| 2016/0375161 A1* | 12/2016 | Hawkins | H05B 33/0854 422/22 |
| 2016/0375162 A1 | 12/2016 | Many | |
| 2016/0375163 A1 | 12/2016 | Hawkins et al. | |
| 2017/0006685 A1 | 1/2017 | Barron et al. | |
| 2017/0034889 A1 | 2/2017 | Primous et al. | |
| 2017/0080117 A1 | 3/2017 | Gordon | |
| 2017/0101326 A1 | 4/2017 | Zhou | |
| 2017/0101328 A1 | 4/2017 | Smetona et al. | |
| 2018/0121703 A1 | 5/2018 | Jung | |
| 2018/0225498 A1 | 8/2018 | Setlak | |

FOREIGN PATENT DOCUMENTS

| | | |
|---|---|---|
| WO | WO2007012875 | 2/2007 |
| WO | WO 2009/056838 | 5/2009 |

OTHER PUBLICATIONS

Maclean et al., "An Innovation: Decontamination by Light—HINS-light Environmental Decontamination System, A new method for pathogen control in the clinical environment," Microsoft Power Point, HINS-light EDS Presentation for Infection Prevention Scotland, The Robertson Trust Laboratory for Electronic Sterilisation Technologies (ROLEST), Oct. 27, 2010—20 pages.

Noimark et al., "Light-activated antimicrobial surfaces with enhanced efficacy induced by a dark-activated mechanism," Chemical Science, Issue 6, Jun. 1, 2014—1 page.

Wallace, John "HINS light kills surface bacteria in hospitals," Laser Focus World, http://www.laserfocusworld.com/articles/2010/11/hins-light-kills-surface.html, accessed on Oct. 30, 2017, PennWell Corporation, Tulsa, OK, Nov. 15, 2010—2 pages.

Maclean et al., Environmental decontamination of a hospital isolation room using high-intensity narrow-spectrum light, The Hospital Infection Society, Elsevier Ltd., Nov. 2010;76(3)—1 page.

Kenall Mfg. Launches New Bacteria-killing LED Light for Hospitals, LEDinside, a Business Division of TrendForce Corp., Jun. 29, 2015, accessed on Oct. 30, 2017, http://www.ledinside.com/products/2015/6/kenall_manufacturing_launches_new_uv_led_light_for_hospitals—3 pages.

Nitzan et al. "ALA induced photodynamic effects on Gram positive and negative bacteria," *Photochem. Photobiol. Sci.*, 2004, 3-18 pages.

MacLean "An Investigation Into the Light Inactivation of Medically Important Microorganisms," University of Strathclyde, 2006—260 pages.

Nitzan et al., "Endogenous Porphyrin Production in Bacteria by Aminolaevulinic Acid and Subsequent Bacterial Photoeradication," *M. Lasers Med Sci* (Dec. 1999) vol. 14, Issue 4, pp. 269-277.

Ashkenazi et al., "Eradication of Propionibacterium acnes by its endogenic porphyrins after illumination with high intensity blue light," *FEMS Immunology & Medical Microbiology*, vol. 35, Issue 1, Jan. 1, 2003, pp. 17-24.

Ganz et al., "*Helicobacter pylori* in Patients Can Be Killed by Visible Light," *Lasers Surg Med.*, Apr. 2005; 36(4): pp. 260-265.

Møller et al., "How Finsen's light cured lupus vulgaris," *Photodermatol Photoimmunol Photomed* 2005; 21: pp. 118-124.

Kjeldstad, "Photoinactivation of Propionibacterium acnes by Near-Ultraviolet Light," *Zeitschrift für Naturforschung C*, vol. 39, Issue 3-4, 1984, pp. 300-302.

Derosa et al., "Photosensitized singlet oxygen and its applications," *Coordination Chemistry Reviews*, vols. 233-234, Nov. 1, 2002, pp. 351-371.

Elman et al., "The effective treatment of acne vulgaris by a high-intensity, narrow band 405-420 nm light source," *J Cosmetic & Laser Ther* 2003; 5: pp. 111-116.

Konig et al., "Red Light Kills Bacteria via Photodynamic Action," Abstract, *Cellular and molecular biology*, 46(7):1297-303, Dec. 2000—1 page.

Philipp-Dormston et al., "Comparison of Porphyrin and Heme in Various Heterotrophic Bacteria," Abstract, *Enzyme* 16(1):57-64 • Feb. 1973—1 page.

* cited by examiner

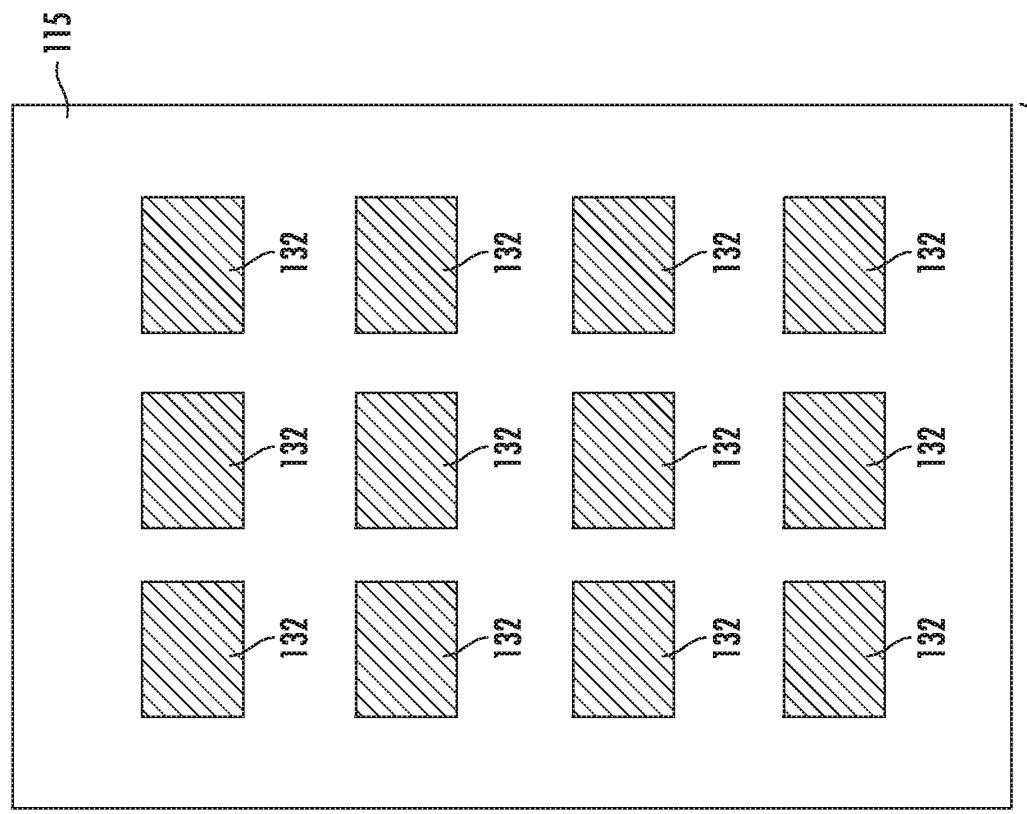
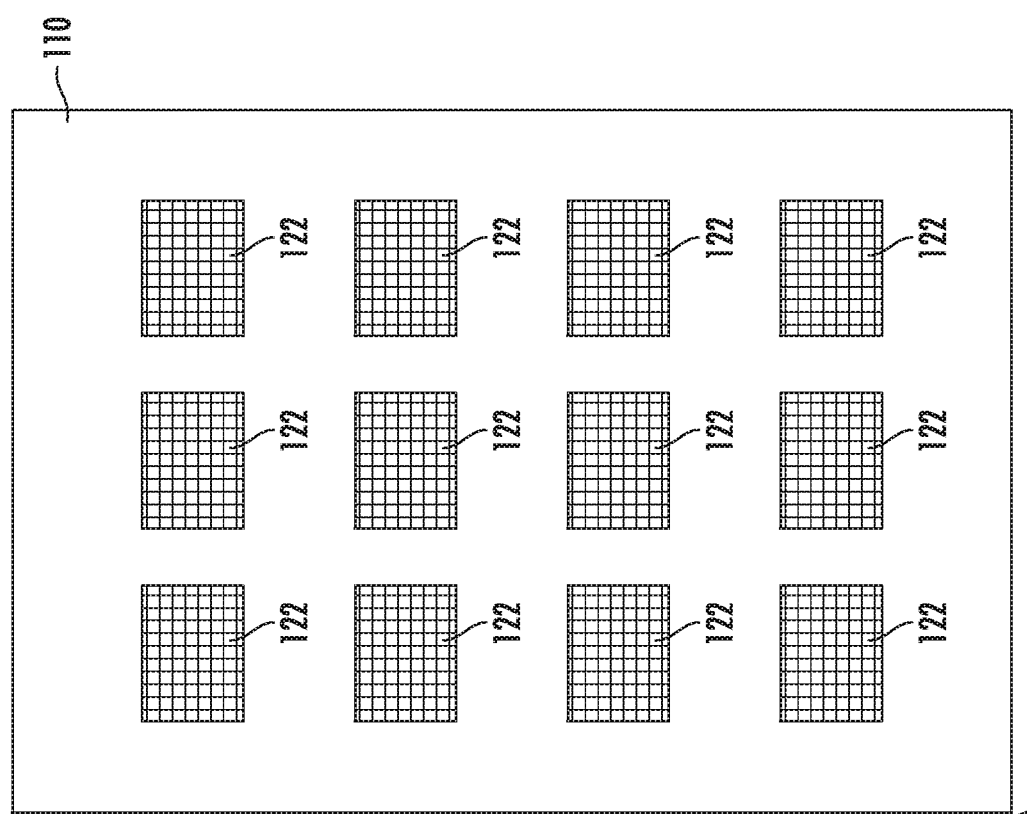
FIG. 3

MULTI-ARRAY LIGHTING SYSTEM FOR PROVIDING HIGH INTENSITY NARROW SPECTRUM LIGHT

PRIORITY CLAIM

The present application claims the benefit of priority of U.S. Provisional Patent Application No. 62/414,987, entitled "Multi-Array LED System for Providing High Intensity Narrow Spectrum Light," filed Oct. 31, 2016, which is incorporated herein by reference for all purposes.

FIELD

The present subject matter relates generally to lighting systems.

BACKGROUND

Lighting systems can be used to provide illumination of spaces and objects for a variety of different applications. In some lighting systems, high intensity narrow spectrum (HINS) light can be used to reduce, suppress, and/or inactivate bacterial or other microorganisms. For instance, HINS light having at least one peak wavelength in the range of about 380 nanometers (nm) to about 420 nm (e.g., 405 nm) has been shown to inactivate certain microorganisms, such as certain gram-positive bacteria.

SUMMARY

Aspects and advantages of embodiments of the present disclosure will be set forth in part in the following description, or may be learned from the description, or may be learned through practice of the embodiments.

One example aspect of the present disclosure is directed to a lighting system. The lighting system can include one or more first light sources to emit high intensity narrow spectrum (HINS) light. The lighting system can include one or more second light sources configured to emit non-HINS light. The system can include a power circuit configured to provide power to the one or more first light sources and the one or more second light sources.

Other example aspects of the present disclosure are directed to systems, methods, devices, circuits and apparatus for providing high intensity narrow spectrum light.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which:

FIG. 3 depicts an example LED arrangement according to example embodiments of the present disclosure;

DETAILED DESCRIPTION

Figure 1:
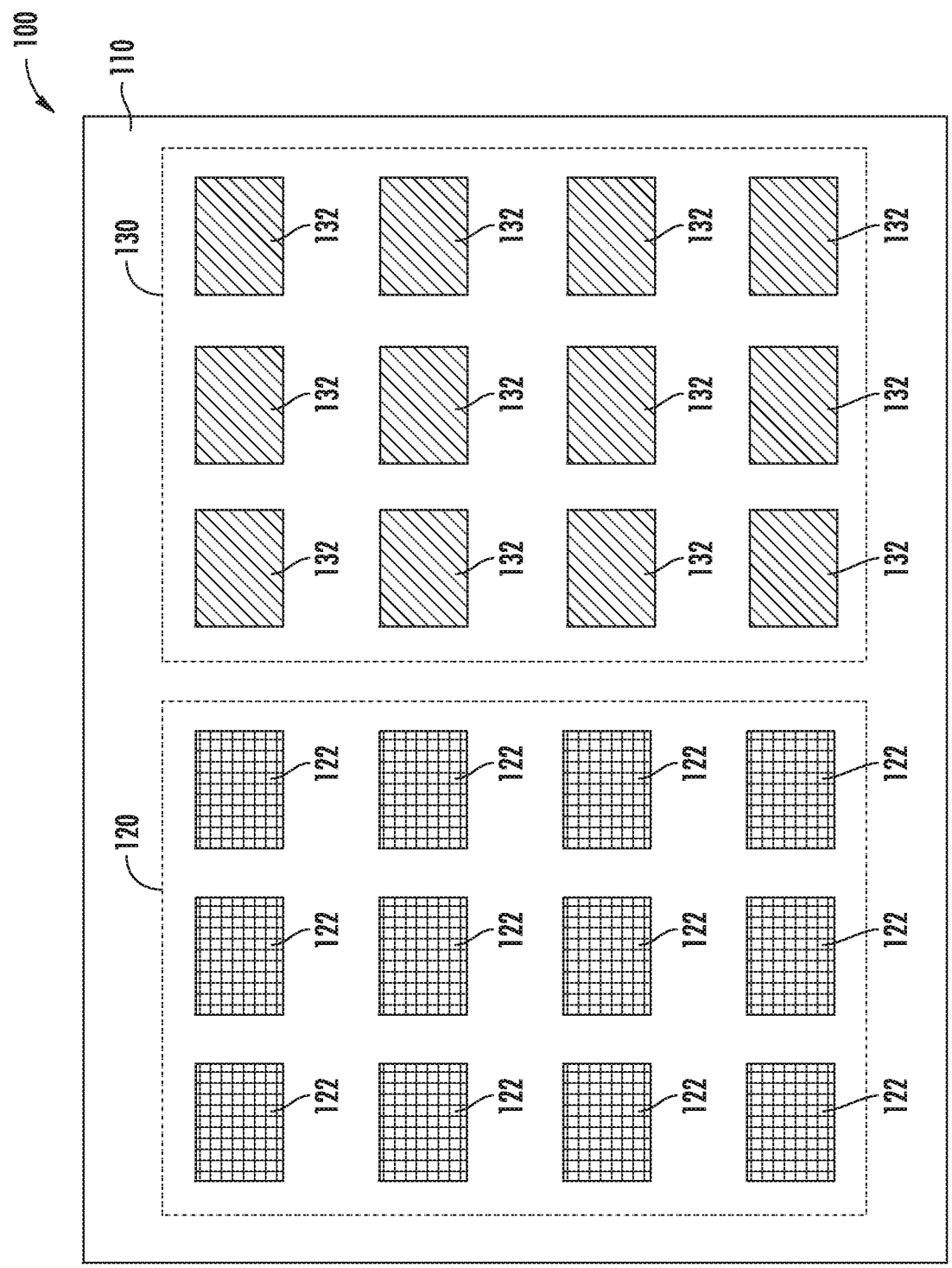
FIG. 1 depicts an example LED arrangement according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed light emitting diode (LED) systems for providing high intensity narrow spectrum (HINS) light. A lighting system can be used to illuminate a space and/or surface with HINS light for a variety of purposes, including antimicrobial purposes. The HINS light can include, for instance, light having a peak wavelength in the range of about 380 nanometers (nm) to about 420 nm, such as about 400 nm to about 420 nm, such as about 405 nm. In some embodiments, HINS light can be emitted into a space or surface for antimicrobial purposes (e.g., to reduce, eliminate, or inactive bacterial, fungal, viral, and/or other microorganism contamination on various surfaces or in various spaces). As will be understood by those skilled in the art, using the disclosures provided herein, HINS light can provide antimicrobial qualities to surfaces upon which the light is emitted. In this manner, the HINS light can reduce, eliminate, suppress and/or inactivate bacterial, fungal, viral, and/or other microorganism contamination on such surfaces.

According to example embodiments, a lighting system can include one or more HINS light sources (e.g., a HINS LED array) to emit HINS light and one or more non-HINS light sources (e.g., a non-HINS LED array) configured to emit non-HINS light. The non-HINS light sources can be configured to emit non-HINS light associated different color temperatures, different intensities, different monochromatic color (e.g., narrow banded colors) or other suitable characteristics.

In some embodiments, the HINS light sources can be solid state light sources, such as one or more HINS LEDs configured to emit HINS light as a result of electrons moving through a semiconductor material. The non-HINS light sources can be solid state light sources, such as one or more non-HINS LEDs configured to emit non-HINS light as a result of electrons moving through a semiconductor material.

In some embodiments, the HINS LED devices and the non-HINS LED devices can be implemented on different circuit boards or on the same circuit board. In some embodiments, the HINS LED devices and the non-HINS LED devices can be implemented as part of the same LED package or different LED packages.

For example, the lighting system can include a multi-die LED arrangement having a plurality of LED dies. The plurality of LED dies can include a first set of one or more LED dies associated with HINS LEDs configured to emit HINS light. The plurality of LED dies can include a second set of one or more LED dies associated with non-HINS LEDs configured to emit non-HINS light. The plurality of LED dies can be implemented as part of the same LED package or different LED packages. The plurality of LED dies can be implemented on the same circuit board or on different circuit boards.

In some embodiments, the HINS LEDs and non-HINS LEDs can be arranged and/or controlled to provide a desired combined light output, such as white light of a desired color temperature (e.g., 4000 K). As an example, a static white combined light output having a color temperature of about 4000 K with Duv of less than about 0.003 can be obtained using LEDs associated with complimentary peak wavelengths of about 405 nm for the HINS LEDs and about 573 nm for the non-HINS LEDs. Non-HINS LEDs associated with different wavelengths can be used in combination with the HINS LEDs to provide for increased flexibility in emitting light over a range of color temperatures.

For example, a dynamic white light color temperature can be obtained using LED associated with peak wavelengths of about 405 nm for the HINS LEDs and about 525 nm and 640 nm for the non-HINS LEDs. This can be extended to an nth number of peak wavelength LEDs to provide a larger color gamut, which in turn, can improve color rendering index. In these embodiments, the HINS LEDs can emit HINS light (e.g., continuously emit HINS light) for antimicrobial purposes while the non-HINS LEDs emit light so that the collective light emitted by the LEDs appears white or other desired color and/or color temperature.

In some embodiments, each LED device or set of LED devices can be individually controlled to provide various lighting effects. For example, the LED devices can be controlled to emit a desired mixture of HINS light and non-HINS light based on the type of lighting application, environment, time of day, and other factors. In some embodiments, smart control functionality can be provided to provide for the controlled emission of light at specific wavelengths from each individual device or set of devices, including emission of HINS light from HINS LED devices, based on measurements from sensors (e.g., motion sensors, temperature sensors, microphones, and others) and other control methods. For instance, the emission of light from a HINS LED device can be triggered only when required, for instance, based on occupancy/vacancy, time delay, controlled occupancy, etc.

In some embodiments, the HINS LED devices and non-HINS LED devices can be controlled to provide for the emission of combined light of a desired color temperature that changes based on various circumstances or parameters. As an example, in some embodiments, color temperature of the combined light emitted by the HINS LED devices and non-HINS LED devices can be controlled over time based on a real time clock to adjust the color temperature over time (e.g., to match a sunlight cycle or other predefined color temperature change profile).

In some embodiments, the color temperature or other characteristics of the combined light can be controlled based on data indicative of user preferences. For instance, if a user prefers a more bluish color temperature, the HINS LED devices and non-HINS LED devices can be controlled to provide a combined light output with a more bluish color temperature. If a user prefers a more reddish color temperature, the HINS LED devices and non-HINS LED devices can be controlled to provide a combined light output with a more reddish color temperature. The data indicative of user preferences can be obtained or accessed from, for instance, user devices (e.g., smartphones, tablets, fitness trackers) carried by a user and communicated to a lighting system over a suitable communication medium or media.

In some embodiments, the HINS LED devices can be combined with other types of light sources. For example, in some embodiments, a lighting system can include one or more UV light sources to provide for aantimicrobial/sterilization capabilities.

In some embodiments, the HINS LED devices and the non-HINS LED devices can be associated with different optics to provide for different lighting distributions of the HINS LED devices and the non-HINS LED devices. For instance, light from the HINS LED devices can be emitted through an optic to provide a first distribution of HINS light. Light from the non-HINS LEDs can be emitted through a different optic to provide a second distribution of non-HINS light. The second distribution can be different than the first distribution.

As used herein, a lighting system can include, but is not limited to, one or more of a lighting circuit, light engine, one or more luminaires, one or more lighting fixtures, one or more lighting units, a plurality of lighting devices arranged in an environment, a combination of any of the foregoing, etc. HINS light refers to light having at least one peak wavelength in the range of about 380 nanometers (nm) to about 420 nm, such as about 400 nm to about 420 nm, such as about 405 nm. Non-HINS light refers to light in the visible spectrum, but not in the HINS range of 380 nm to 405 nm. An LED device can include an LED die, an LED package, an LED package having multiple dies, an arrangement of LED dies, an arrangement of LED packages, an LED array, or other suitable combination of one or more devices configured to emit light as a result of electrons moving through a semiconductor material. The use of the term "about" in conjunction with a numerical value refers to within 5% of the stated numerical value.

Example aspects of the present disclosure are discussed with reference to an LED lighting system for purposes of illustration and discussion. Those of ordinary skill in the art, using the disclosures provided herein, will understand that a lighting system according to example aspects of the present disclosure can include other types of light sources.

FIG. 1 depicts an example LED arrangement 100 according to example embodiments of the present disclosure. The LED arrangement 100 includes a plurality of LED devices, including a first set of LED devices 120 and a second set of LED devices 130. Each LED device can be configured to emit light as a result of electrons moving through a semiconductor material.

The first set of LED devices 120 can include HINS LED devices 122 configured to emit HINS light. For instance, the one or more HINS LED devices 122 can be configured to emit HINS light or can include one or more coatings, lenses, materials, etc. that transform light emitted by the LED devices into HINS light.

The second set of LED devices 130 can include one or more non-HINS LED devices 132 configured to emit non-HINS light of any suitable color and/or color temperature. For instance, the LED devices 132 can be configured to emit light having a peak wavelength that is different from a peak wavelength in the HINS range. In some embodiments, the peak wavelength of the LED devices 132 can be selected such that a combined light output of the LED arrangement 100 is of a desired color and/or color temperature.

As shown in FIG. 1, the first set of LED devices 120 and the second set of LED devices 130 are implemented on the same circuit board 110. As discussed in detail below, the first set of LED devices 120 and the second set of LED devices 130 can be independently controlled to provide various lighting effects.

Figure 2:
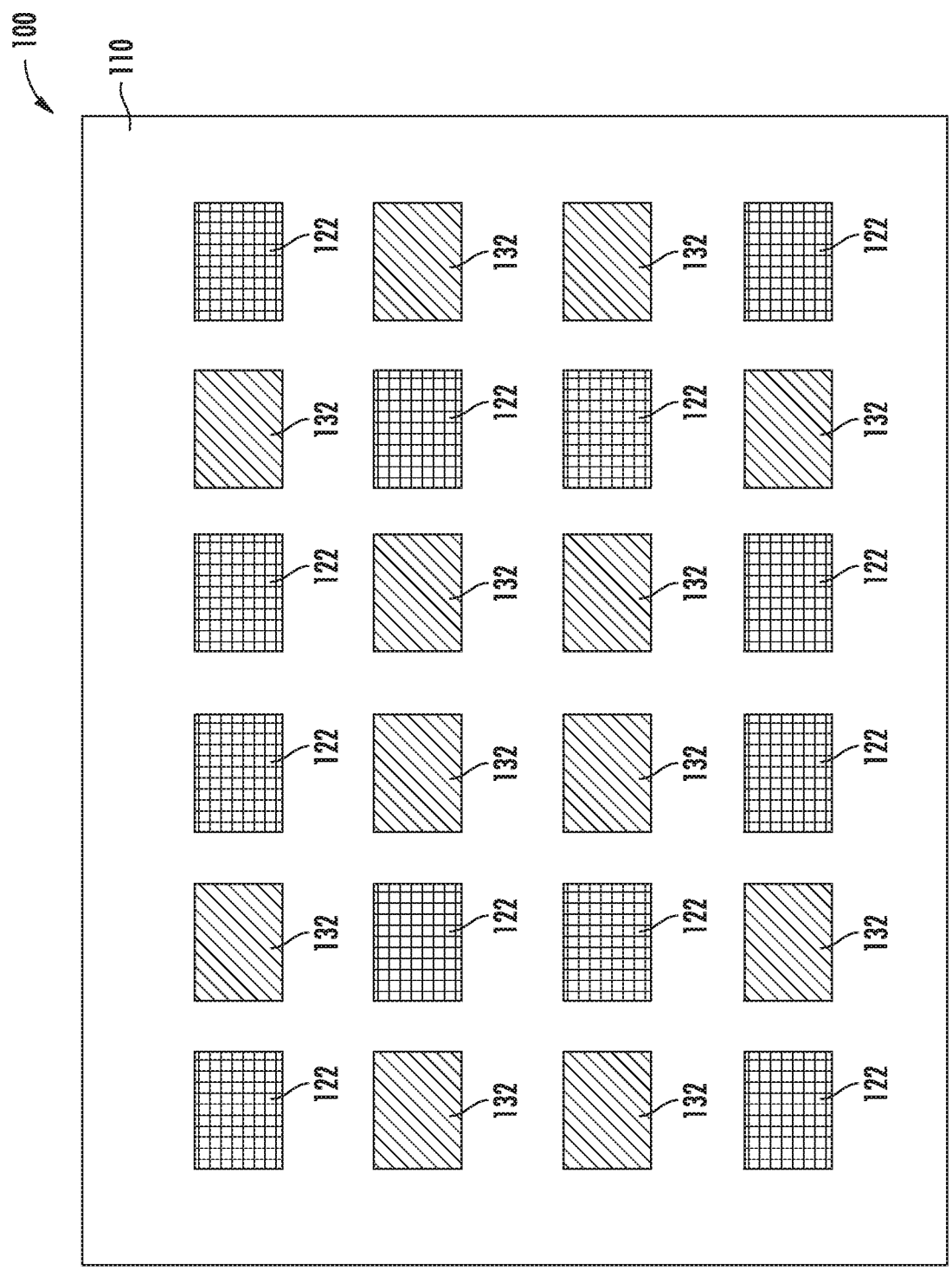
FIG. 2 depicts an example LED arrangement according to example embodiments of the present disclosure.

FIG. 2 depicts an example LED arrangement 100 according to example embodiments of the present disclosure. The LED arrangement 100 includes a plurality of LED devices, including HINS LED devices 122 and non-HINS LED devices 132. The one or more HINS LED devices 122 can be configured to emit HINS light or can include one or more coatings, lenses, materials, etc. that transform light emitted by the LED devices into HINS light. The one or more non-HINS LED devices 132 can be configured to emit non-HINS light of any suitable color and/or color temperature. For instance, the non-HINS LED devices 132 can be configured to emit light having a peak wavelength that is different from a peak wavelength in the HINS range. In some embodiments, the peak wavelength of the non-HINS LED devices 132 can be selected such that a combined light output of the LED arrangement 100 is of a desired color and/or color temperature. As an example, a static white combined light output having a color temperature of about 4000 K with Duv of less than about 0.003 can be obtained using LEDs associated with complimentary peak wavelengths of about 405 nm for the HINS LEDs and about 573 nm for the non-HINS LEDs.

Similar to the LED arrangement of FIG. 1, the HINS LED devices 122 and the non-HINS LED devices 132 are implemented on the same circuit board 110. However, the HINS LED devices 122 and the non-HINS LED devices 132 are interspersed according to an LED distribution pattern. The LED distribution pattern can be configured such that the combined light output of the HINS LED devices 122 and the non-HINS LED devices 132 is of a desired color and/or color temperature. Any suitable LED distribution can be used without deviating from the scope of the present disclosure.

FIG. 3 depicts an example LED arrangement 100 according to example embodiments of the present disclosure. The LED arrangement 100 includes a plurality of LED devices, including HINS LED devices 122 and non-HINS LED devices 132. The HINS LED devices 122 can be configured to emit HINS light or can include one or more coatings, lenses, materials, etc. that transform light emitted by the LED devices into HINS light. The non-HINS LED devices 132 can be configured to emit non-HINS light of any suitable color and/or color temperature. For instance, the non-HINS LED devices 132 can be configured to emit light having a peak wavelength that is different from a peak wavelength in the HINS range.

The HINS LED devices 122 and the non-HINS LED devices 132 are implemented on different circuit boards. For instance, HINS LED devices 122 are implemented on a first circuit board 110. The non-HINS LED devices 132 are implemented on a second circuit board 115. The LED arrangement can be implemented across any number of circuit boards without deviating from the scope of the present disclosure.

Figure 4:
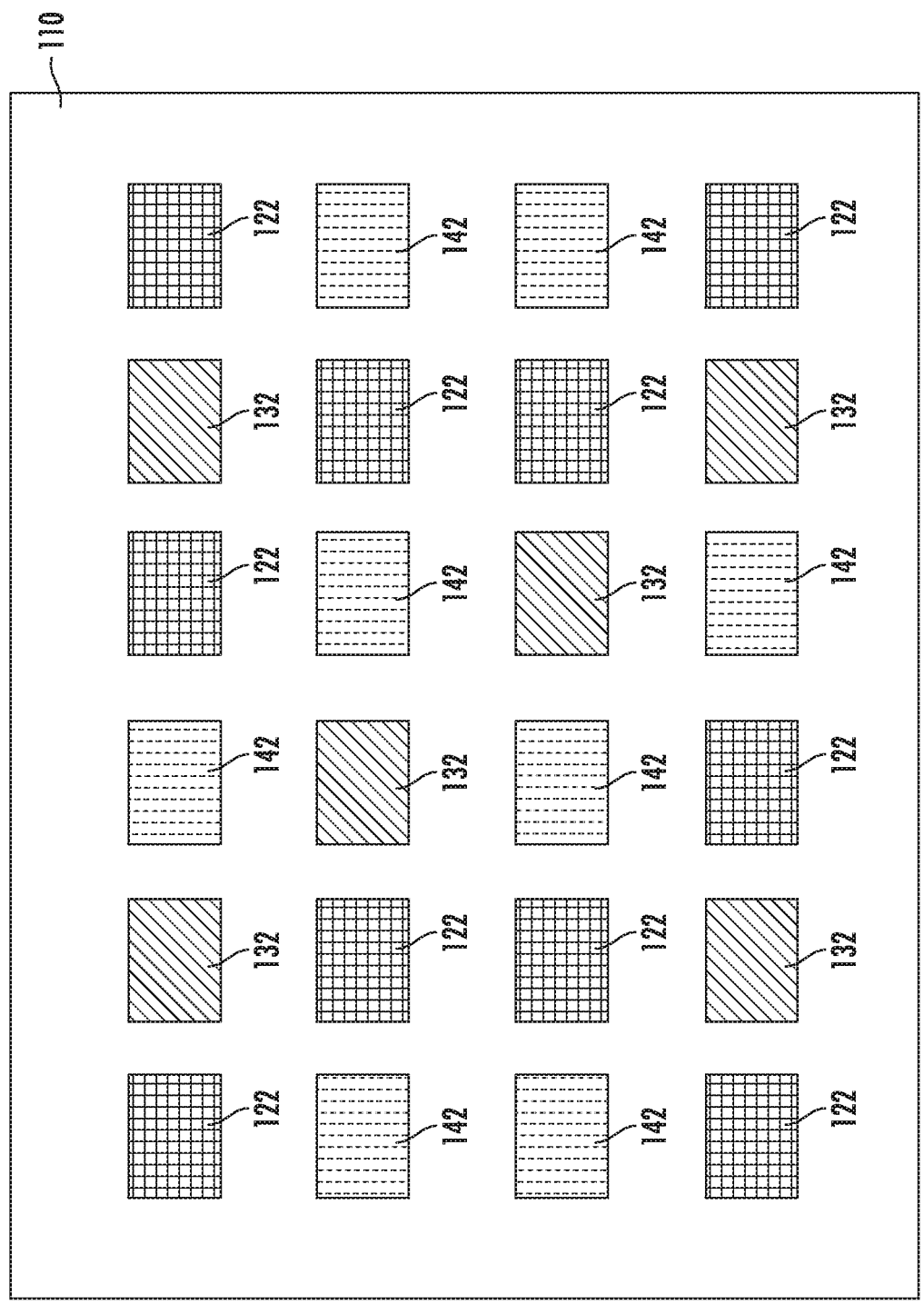
FIG. 4 depicts an example LED arrangement according to example embodiments of the present disclosure.

FIG. 4 depicts an example LED arrangement 100 according to example embodiments of the present disclosure. The LED arrangement 100 includes a plurality of LED devices, including HINS LED devices 122, first non-HINS LED devices 132, and second non-HINS LED devices 142. The HINS LED devices 122 can be configured to emit HINS light or can include one or more coatings, lenses, materials, etc. that transform light emitted by the LED devices into HINS light.

The first non-HINS LED devices 132 can be configured to emit non-HINS light of any suitable color and/or color temperature. For instance, the first non-HINS LED devices 132 can be configured to emit light having a peak wavelength that is different from a peak wavelength in the HINS range.

The second non-HINS LED devices 142 can be configured to emit non-HINS light of any suitable color and/or color temperature. For instance, the second non-HINS LED devices 142 can be configured to emit light having a peak wavelength that is different from a peak wavelength in the HINS range.

In some embodiments, the peak wavelength of the first non-HINS LED devices 132 and the second non-HINS LED devices 142 can be selected such that a combined light output of the LED arrangement 100 is of a desired color and/or color temperature. For example, a dynamic white light color temperature can be obtained using LED associated with peak wavelengths of about 405 nm for the HINS LEDs and about 525 nm and 640 nm for the non-HINS LEDs. Non-HINS LEDs associated with different wavelengths can be used in combination with the HINS LEDs to provide for increased flexibility in emitting light over a range of color temperatures.

Any suitable number of different types of non-HINS LED devices can be used without deviating from the scope of the present disclosure.

The HINS LED devices 122, the first non-HINS LED devices 132 and the second non-HINS LED devices 142 are implemented on the same circuit board 110. The HINS LED devices 122, the first non-HINS LED devices 132, and the second non-HINS LED devices are interspersed according to an LED distribution pattern. The LED distribution pattern can be configured such that the combined light output of the LED arrangement 100 is of a desired color and/or color temperature. Any suitable LED distribution can be used without deviating from the scope of the present disclosure.

FIGS. 1 to 4 depict example LED arrangements having a plurality of HINS LED devices and non-HINS LED devices for purposes of illustration and discussion of example embodiments. Those of ordinary skill in the art, using the disclosures provided herein, will understand that a variety of different LED arrangements including one or more HINS LED devices and non-HINS LED devices can be used without deviating from the scope of the present disclosure.

According to example embodiments of the present disclosure, the one or more HINS LED devices and the one or more non-HINS LED devices can be controlled to provide various lighting effects or other control functionality. Example lighting systems providing for independent control of one or more HINS light sources and one or more non-HINS light sources are discussed in detail below.

Figure 5:
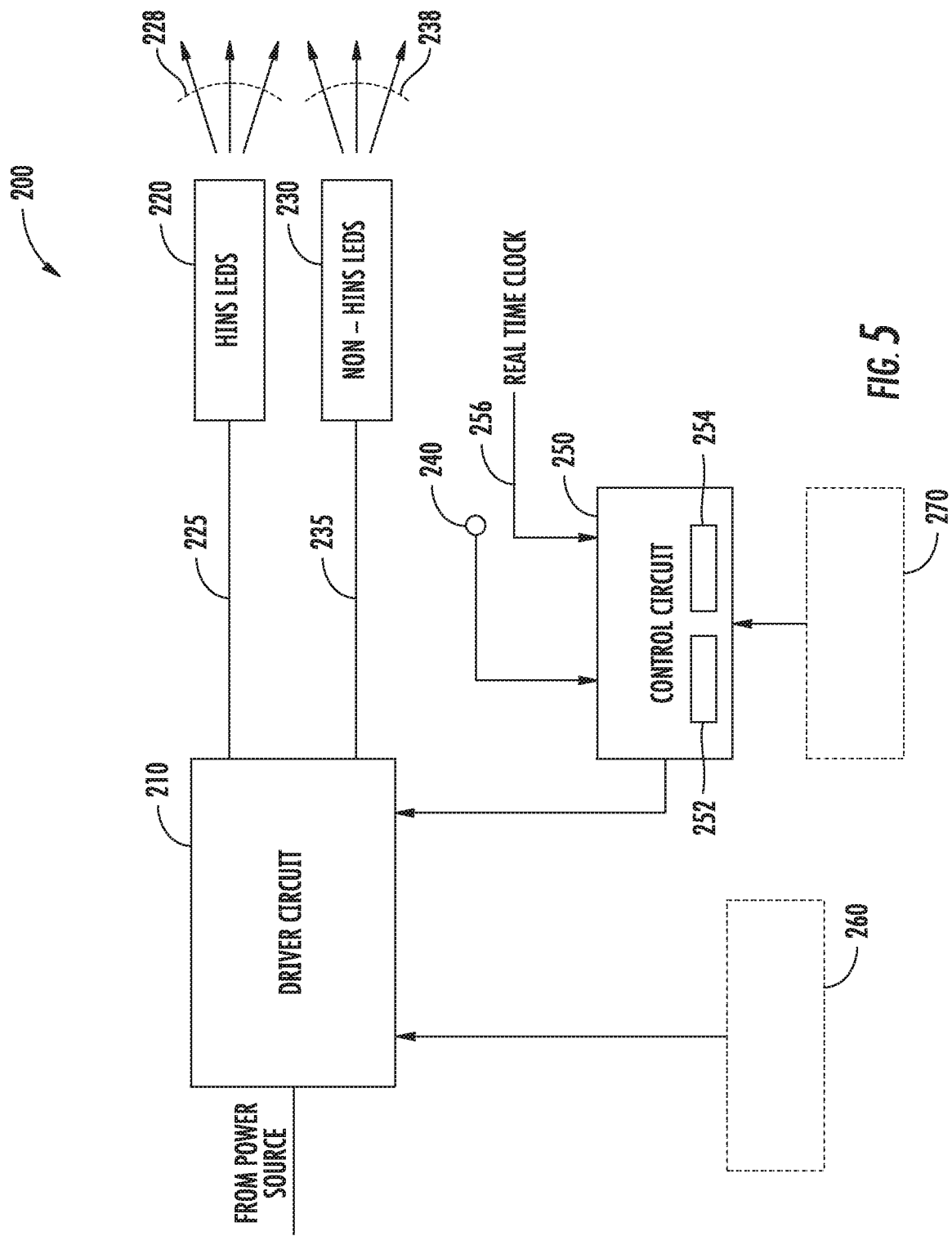
FIG. 5 depicts an example lighting system according to example embodiments of the present disclosure.

FIG. 5 depicts an example implementation of an LED lighting system 200 configured to provide HINS light according to example aspects of the present disclosure. The LED lighting system 200 includes an LED driver circuit 210, a control circuit 250, and one or more HINS LED devices 220 configured to emit HINS light and one or more non-HINS LED devices 230 (e.g., a non-HINS LED array) configured to emit non-HINS light. The one or more HINS LED devices 220 and non-HINS LED devices 230 can be arranged in any suitable manner, such as similar to the LED arrangements illustrated in FIGS. 1-4. The lighting system 200 can include other light sources without deviating from the scope of the present disclosure.

As shown in FIG. 5, in some embodiments, the HINS LED devices 220 can emit light through a first optic 228 so as to provide light associated with a first distribution. The non-HINS LED devices 230 can emit light through a second optic 238 so as to provide light associated with a second distribution. The first distribution can be different from the second distribution. In this way, the distribution of HINS light relative to non-HINS light in a lighting system can be more specifically controlled, for instance, to illuminate specific surfaces for antimicrobial purposes. The non-HINS light sources can provide light using a distribution to provide general illumination for a space and/or surface.

The driver circuit 210 can be, for instance, any suitable driver circuit 210 configured to convert an input power (e.g., an input AC or DC power) to a suitable driver output (e.g. driver current) for powering the HINS LED devices 220 and the non-HINS LED devices 230. In some embodiments, the driver circuit 210 can be a dimmable driver circuit. The driver circuit 210 is illustrated as a multichannel driver circuit configured to power HINS LED devices 220 over a first channel 225 and to power non-HINS LED devices 230 over a second channel 235. Other suitable arrangements can be used to provide power to the HINS LED devices 220 and non-HINS LED devices 230 without deviating from the scope of the present disclosure. For instance, independent driver circuits can be used to power the HINS LED devices 220 and the non-HINS LED devices 230. In some embodiments, the driver circuit 210 can be implemented on the same circuit board as the HINS LED devices 220 and/or the non-HINS LED devices 230.

In some embodiments, the dimmable driver circuit 210 can include various components, such as switching elements (e.g. transistors) that are controlled to provide a suitable driver output. For instance, in some example embodiments, the driver circuit 210 can include one or more transistors. Gate timing commands can be provided to the one or more transistors to convert the input power to a suitable driver output using pulse width modulation techniques. In some example embodiments, the dimmable driver circuit 210 can be a line dimming driver, such as a phase-cut dimmable driver, Triac dimmer, trailing edge dimmer, or other line dimming driver. The driver output can be adjusted using the line dimming driver by controlling the input power to the dimmable driver circuit 210.

In some embodiments, an interface 260 can be provided at the driver circuit 210 for receiving a dimming control signal used to control the driver output. The interface 260 can include one or more components for communicating a dimming control signal to the driver circuit 210. For example, the interface 260 can include one or more circuits, terminals, pins, contacts, conductors, or other components for communicating a dimming control signal to the driver circuit 210.

The dimming control signal can be provided from an external circuit, such as an external dimming circuit or external control device. The external circuit can include one or more devices, such as a smart dimming interface, a potentiometer, a Zener diode, or other device. In some embodiments, the dimming control signal can be received from the control circuit 250. In one example implementation, the dimming control signal can be a 0V to 10V dimming control signal. The dimming control signal can be implemented using other suitable protocols, such as a DALI protocol, or a DMX protocol.

In some embodiments, the dimming control signal can be received from a remote device over a wireless communication medium or other communication medium. Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

The control circuit 250 can be configured to control the delivery of power to the HINS LED devices 220 and the non-HINS LED devices 230 from the driver circuit 210 to provide various lighting effects, such as for providing a combined light output from the HINS LED devices 220 and the non-HINS LED devices 230 of a desired color and/or color temperature or other lighting effect. For example, the control circuit 250 can independently control the driver output provided over channel 225 and 235 so that the light output of the HINS LED devices 220 and non-HINS LED devices can be independently controlled to achieve desired lighting effects.

As illustrated, the control circuit 250 can include one or more processors 252 and one or more memory devices 254. The one or more memory devices 254 can store computer-readable instructions that when executed by the one or more processors 252 cause the one or more processors to provide control functionality according to example aspects of the present disclosure. For instance, the one or more memory devices 254 can store computer-readable instructions that when executed by the one or more processors 252 cause the control circuit 250 to control the light output of the lighting system according to one or more control schemes. The control schemes can be pre-programmed into the memory devices 254 or may be programmed by a user from time-to-time in one or memory devices 254 using a suitable user interface. Example control schemes are discussed in detail below.

The control circuit 250 can be implemented on the same circuit board as the driver circuit 210 or can be located remote from the driver circuit 210 and/or the lighting system 200. In some embodiments, the control circuit 250 can control the driver circuit 210 over a suitable communication medium, such as a wired or wireless communication medium.

In some embodiments, the control circuit 250 can include an interface 270 for receiving a lighting control signal or other control signal. The interface 270 can include one or more components for communicating the lighting control signal to the control circuit 250. For example, the interface 270 can include one or more circuits, terminals, pins, contacts, conductors, transmitters, receivers, transceivers, or other components for communicating the lighting control signal.

In some embodiments, the interface 270 can receive a lighting control signal over a wireless communication interface. Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

The control circuit 250 and/or lighting control signal can specify control of the lighting system 200 (e.g., the amount of driver output to provide to the HINS LED devices 220 and the non-HINS LED devices 230) based on various parameters and/or control schemes to provide smart control functionality. For example, the control circuit 250 can receive signals from one or more sensors 240 (e.g., optical sensors, motion sensors, etc.) and control light output of the HINS LEDs 220 and the non-HINS LEDs 230 so that the light output of the lighting system 200 meets desired requirements (e.g., a specified amount of HINS light for antimicrobial purposes).

As another example, control circuit 250 can adjust the combined light output of the lighting system according to a defined light profile based at least in part on a signal 256 associated with a real time clock. The defined light profile can specify an adjustment in the color temperature and/or other characteristics collective light output over time based at least in part on entrainment of a circadian rhythm of a living organism exposed to the light output and/or based on user settings or preferences. For instance, in some embodiments, the defined light profile can be defined at least in part on a natural day/night cycle.

As another example, the color temperature or other characteristics of the combined light can be controlled based on data indicative of user preferences. For instance, if a user prefers a more bluish color temperature, the HINS LED devices and non-HINS LED devices can be controlled to provide a combined light output with a more bluish color temperature. If a user prefers a more reddish color temperature, the HINS LED devices and non-HINS LED devices can be controlled to provide a combined light output with a more reddish color temperature. The data indicative of user preferences can be obtained or accessed from, for instance, user devices (e.g., smartphones, tablets, fitness trackers) carried by a user and communicated to a lighting system over a suitable communication medium or media.

Figure 6:
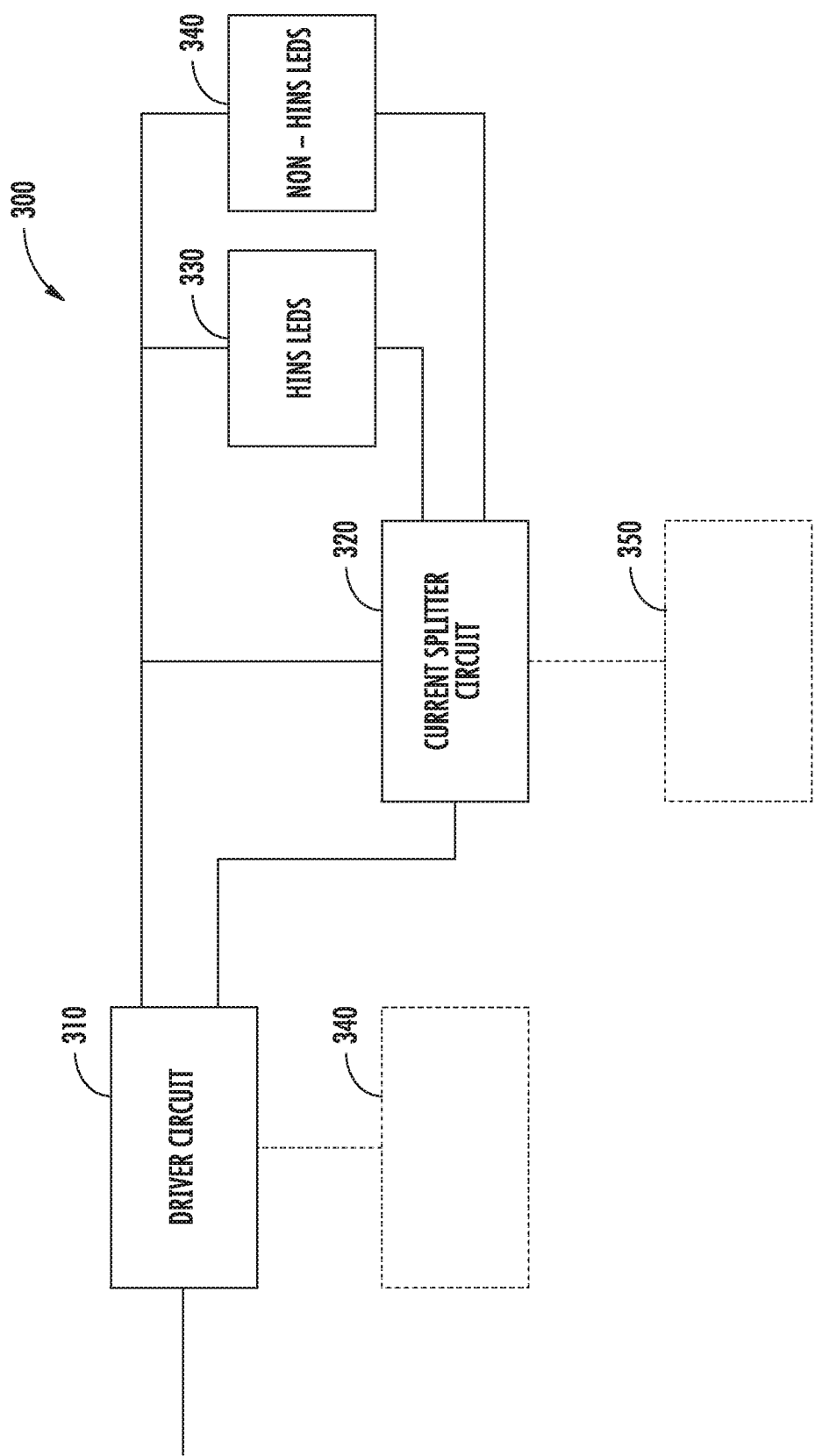
FIG. 6 depicts an example lighting system according to example embodiments of the present disclosure.

Other suitable arrangements can be used for controlling the light output of HINS LED devices and non-HINS LED devices to achieve desired lighting effects. For instance, FIG. 6 depicts a block diagram of an LED lighting system 300 according to example embodiments of the present disclosure. The LED lighting system 300 includes a current splitter circuit for controlling the distribution of power among HINS LED devices and non-HINS LED devices.

More particularly, the lighting system 300 can include an LED driver circuit 310, a current splitter circuit 320, one or more HINS LED devices 330 and one or more non-HINS LED devices 340. The one or more HINS LED devices 220 and non-HINS LED devices 230 can be arranged in any suitable manner, such as similar to the LED arrangements illustrated in FIGS. 1-4. The lighting system 200 can include other light sources without deviating from the scope of the present disclosure.

The LED driver circuit 310 can be configured to receive an input power, such as an input AC power or an input DC power, and can convert the input power to a suitable driver output (e.g. driver current) for powering the plurality of LED arrays. In some embodiments, the driver circuit 310 can be a dimmable driver circuit. The dimmable driver circuit 310 can include various components, such as switching elements (e.g. transistors) that are controlled to provide a suitable driver output. For instance, in one embodiment, the driver circuit 310 can include one or more transistors. Gate timing commands can be provided to the one or more transistors to convert the input power to a suitable driver output using pulse width modulation techniques. In some example embodiments, the dimmable driver circuit 510 can be a line dimming driver, such as a phase-cut dimmable driver, Triac dimmer, trailing edge dimmer, or other line dimming driver. The driver output can be adjusted using the line dimming driver by controlling the input power to the dimmable driver circuit.

In addition and/or in the alternative, a first interface 340 can be provided at the dimmable driver circuit 310 for receiving a dimming control signal used to control the driver output. The first interface 340 can include one or more components for communicating the dimming control signal to the driver circuit 310. For example, the first interface 340 can include one or more circuits, terminals, pins, contacts, conductors, receivers, transmitters, transceivers, or other components for communicating the dimming control signal to the driver circuit 310.

The dimming control signal can be provided from an external circuit, such as an external dimming circuit. The external circuit can include one or more devices, such as a smart dimming interface, a potentiometer, a Zener diode, or other device. In one example implementation, the dimming control signal can be a 0V to 10V dimming control signal, depending on the output of the external circuit. For instance, if a user manually adjusts a dimmer, the dimming control signal can be adjusted from, for instance, 0V to 5V. The dimming control signal can be implemented using other suitable protocols, such as a digital addressable lighting interface (DALI) lighting control signal, digital multiplex (DMX) lighting control signal, or other suitable protocol.

In some embodiments, the dimming control signal can be received from a remote device over a wireless communication medium or other communication medium. Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

The driver circuit 310 can be configured to adjust the driver output based at least in part on the dimming control signal. As a result, the light output of the HINS LED devices 330 and the non-HINS LED device 340 can be simultaneously adjusted (e.g. dimmed) by varying the dimming control signal.

As illustrated in FIG. 6, the driver output can be provided to a current splitter circuit 320. The current splitter circuit 320 can be configured to split the driver output into a first current for powering the HINS LED devices 330 and a second current for powering the non-HINS LED devices 340. In this way, the current splitter circuit 520 can be used to adjust the light output of the HINS LED devices 330 relative to the light output of the non-HINS lighting devices 340. The current splitter circuit 320 can be configured to control the current ratio of the first current provided to the HINS LED devices 330 relative to the second current provided to the non-HINS LED devices 340 based on a lighting control signal.

In some embodiments, the current splitter circuit 320 can include one or more switching elements (e.g., transistors) used to control a current provided to the HINS LED devices 330. The current splitter 320 can include one or more switching elements (e.g., transistor) used to a control a current provided to the non-HINS LED devices 340. The switching elements can be controlled using pulse width modulation to split the current from the driver circuit 310 among the HINS LED devices 330 and the non-HINS LED devices 340 according to a lighting control signal.

More particularly, a second interface 350 at the current splitter circuit 320 can receive a lighting control signal (e.g., variable reference signal). The second interface 350 can include one or more components for communicating the variable reference signal to the current splitter circuit 320. For example, the second interface 350 can include one or more circuits, terminals, pins, contacts, conductors, receivers, transmitters, transceivers, or other components for communicating a variable reference signal to the current splitter circuit 320.

The control signal can be provided from an external circuit, such as an external dimming circuit, over for instance, a network. The external circuit can include one or more devices, such as a smart dimming interface, remote control, control interface, a potentiometer, a Zener diode, or other device. The control signal can be a 0V to 10V lighting control signal, depending on the output of the external circuit. The control signal can be implemented using other suitable protocols, such as a DALI protocol, or a DMX protocol.

In some embodiments, the lighting control signal can be received from a remote device over a wireless communication medium or other communication medium. Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

The current splitter circuit 320 can include one or more control devices (e.g. a microprocessor, a microcontroller, logic device, etc.) and one or more switching elements (e.g. transistors) in line with each of the HINS LED devices 330 and the non-HINS LED devices 340. The control device(s) can control the amount of current provided to the HINS LED devices 330 and the non-HINS LED devices 340 by controlling the switching elements. The switching elements used to control the amount of current provided to HINS LED devices 330 and the non-HINS LED devices 340. can be either on the low voltage side of the LED arrays or the high voltage side of the HINS LED devices 330 and the non-HINS LED devices 340.

In particular aspects, the control device(s) can control the current provided to the HINS LED devices 330 and the non-HINS LED devices 340 according to a current ratio control curve based on the variable reference signal. The current ratio control curve can be stored in firmware or stored in a memory accessible by the control device. The current ratio control curve can specify the current ratio of the first current provided to the HINS LED devices 330 and the non-HINS LED devices 340 as a function of at least the control signal.

Similar to the lighting system of FIG. 5, the control device(s) of the current splitter circuit and/or lighting control signal can specify control of the lighting system 300 (e.g., the amount of driver output to provide to the HINS LED devices 330 and the non-HINS LED devices 340) based on various parameters and/or control schemes to provide smart control functionality. For example, the current splitter 320 can receive signals from one or more sensors (e.g., optical sensors, motion sensors, etc.) and can control light output of the HINS LED devices 330 and the non-HINS LED devices 340 so that the light output of the lighting system 300 meets desired requirements (e.g., a specified amount of HINS light for antimicrobial purposes).

As another example, the current splitter circuit 320 can adjust the combined light output of the lighting system according to a defined light profile based at least in part on a signal associated with a real time clock. The defined light profile can specify an adjustment in the color temperature of the collective light output over time based at least in part on entrainment of a circadian rhythm of a living organism exposed to the light output and/or based on user settings or preferences. For instance, in some embodiments, the defined light profile can be defined at least in part on a natural day/night cycle. Other suitable defined light profiles can be used without deviating from the scope of the present disclosure.

As another example, the color temperature or other characteristics of the combined light can be controlled based on data indicative of user preferences. For instance, if a user prefers a more bluish color temperature, the current splitter circuit 320 can be controlled to provide a combined light output with a more bluish color temperature. If a user prefers a more reddish color temperature, the current splitter circuit 320 can be controlled to provide a combined light output with a more reddish color temperature. The data indicative of user preferences can be obtained or accessed from, for instance, user devices (e.g., smartphones, tablets, fitness trackers) carried by a user and communicated to a lighting system over a suitable communication medium or media.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A lighting system, comprising:
   a first circuit board;
   a plurality of first light sources arranged on the first circuit board, the plurality of first light sources configured to emit light having a wavelength in a range of about 380 nanometers (nm) to about 420 nm through a first optic configured to provide a first distribution of light;
   a second circuit board;
   a plurality of second light sources arranged on the second circuit board, the plurality of second light sources configured to emit light having a wavelength outside the range of about 380 nm to about 420 nm through a second optic that is different from the first optic and configured to provide a second distribution of light that is different than the first distribution of light; and
   a power circuit configured to control power to the plurality of first light sources and to the plurality of second light sources.

2. The lighting system of claim 1, wherein:
   the plurality of first light sources comprise a plurality of first LED devices; and the plurality of second light sources comprise a plurality of second LED devices.

3. The lighting system of claim 2, wherein the wavelength of the light emitted by the plurality of first LED devices is in a range of about 400 nm to about 420 nm.

4. The lighting system of claim 2, wherein the wavelength of the light emitted by the plurality of first LED devices is about 405 nm.

5. The lighting system of claim 2, wherein the lighting system further comprises:
a control circuit configured to control the distribution of power among the plurality of first LED devices and the plurality of second LED devices so as to control a combined light output of the plurality of first LED devices and the plurality of second LED devices.

6. The lighting system of claim 1, wherein the lighting system comprises one or more UV light sources.

7. The lighting system of claim 2, wherein the power circuit comprises:
a first driver circuit configured to control power delivery to the plurality of first LED devices; and
a second driver circuit configured to control power delivery to the plurality of second LED devices.

8. The lighting system of claim 1, further comprising:
a circuit configured to convert an input power to an output power for the plurality of first light sources and the plurality of second light sources.

9. The lighting system of claim 8, wherein the circuit is configured to adjust a power distribution amongst the plurality of first light sources and the plurality of second light sources such that 100 percent of the output power is provided to the plurality of first light sources and 0 percent of the output power is provided to the plurality of second light sources.

10. The lighting system of claim 8, wherein the circuit is configured to adjust a power distribution amongst the plurality of first light sources and the plurality of second light sources such that 100 percent of the output power is provided to the plurality of second light sources and 0 percent of the output power is provided to the plurality of first light sources.

11. The lighting system of claim 8, wherein the circuit is configured to adjust a power distribution amongst the plurality of first light sources and the plurality of second light sources such that the output power is split between the plurality of first light sources and the plurality of second light sources.

12. The lighting system of claim 8, wherein:
the plurality of first light sources comprise a plurality of first LED devices; and
the plurality of second light sources comprise a plurality of second LED devices.

13. A lighting fixture, comprising:
a first circuit board;
a plurality of first light sources arranged on the first circuit board, the plurality of first light sources configured to emit light having a wavelength in a range of about 380 nanometers (nm) to about 420 nm through a first optic configured to provide a first distribution of light;
a second circuit board;
a plurality of second light sources arranged on the second circuit board, the plurality of second light sources configured to emit light having a wavelength outside the range of about 380 nm to about 420 nm through a second optic that is different from the first optic and configured to provide a second distribution of light that is different than the first distribution of light; and
a power circuit configured to control power to the plurality of first light sources and to the plurality of second light sources.

14. The lighting fixture of claim 13, further comprising:
a driver circuit configured to receive an input power and convert the input power to a driver output for powering the plurality of first light sources and the plurality of second light sources.

15. The lighting fixture of claim 14, further comprising:
a current splitter circuit configured to split the driver output into a first current for powering the plurality of first light sources and a second current for powering the plurality of second light sources.

16. The lighting fixture of claim 13, wherein the wavelength of the light emitted by the plurality of first light sources is in a range of about 400 nm to about 420 nm.

17. The lighting fixture of claim 16, wherein the wavelength of the light emitted by the plurality of first light sources is about 405 nm.

18. The lighting fixture of claim 13, wherein:
the plurality of first light sources comprise a plurality of first LED devices; and
the plurality of second light sources comprise a plurality of second LED devices.

* * * * *